(12) United States Patent
Kobayashi et al.

(10) Patent No.: US 8,197,425 B2
(45) Date of Patent: Jun. 12, 2012

(54) ANKLE-FOOT ORTHOSIS PRESCRIPTION ASSISTIVE DEVICE

(75) Inventors: Toshiki Kobayashi, Hong Kong (CN);
Kam Lun Leung, Hong Kong (CN);
Yasushi Akazawa, Akashi (JP); Satoru Maeda, Kakogawa (JP); Toshiya Nakamura, Kobe (JP)

(73) Assignee: Hong Kong Polytechnic University, Kowloon (HK)

( * ) Notice: Subject to any disclaimer, the term of this patent is extended or adjusted under 35 U.S.C. 154(b) by 48 days.

(21) Appl. No.: 12/618,096

(22) Filed: Nov. 13, 2009

(65) Prior Publication Data

US 2011/0118630 A1  May 19, 2011

(51) Int. Cl.
*A61B 5/103* (2006.01)
*A61B 5/117* (2006.01)
*A61B 5/04* (2006.01)

(52) U.S. Cl. .......... 600/595; 600/546; 600/587
(58) Field of Classification Search .......... 600/587, 600/592, 595
See application file for complete search history.

(56) References Cited

U.S. PATENT DOCUMENTS

| | | | | |
|---|---|---|---|---|
| 4,236,528 A * | 12/1980 | Stanec et al. | .......... | 600/554 |
| 4,738,269 A | 4/1988 | Nashner | | |
| 5,038,795 A | 8/1991 | Roush et al. | | |
| 5,050,618 A * | 9/1991 | Larsen | .......... | 600/587 |
| 5,297,540 A | 3/1994 | Kaiser et al. | | |
| 5,313,968 A | 5/1994 | Logan et al. | | |
| 5,979,067 A * | 11/1999 | Waters | .......... | 33/512 |
| 5,980,472 A * | 11/1999 | Seyl | .......... | 600/587 |
| 6,045,517 A * | 4/2000 | Williams | .......... | 600/587 |
| 6,219,929 B1 * | 4/2001 | Tasker et al. | .......... | 33/515 |
| 6,409,684 B1 | 6/2002 | Wilk | | |
| 6,589,190 B2 | 7/2003 | Kanderian, Jr. et al. | | |
| 6,599,255 B2 | 7/2003 | Zhang | | |
| 6,792,801 B2 | 9/2004 | Hoggan et al. | | |
| 7,204,814 B2 | 4/2007 | Peles | | |
| 2005/0288609 A1 * | 12/2005 | Warner et al. | .......... | 600/592 |
| 2010/0145233 A1 * | 6/2010 | Zhang et al. | .......... | 600/592 |

OTHER PUBLICATIONS

Chung et al., "Biomechanic Changes in Passive Properties of Hemiplegic Ankles With Spastic Hypertonia", *Arch Phys Med Rehabil*, vol. 85:1638-1646 (2004).

Chung et al., "Biomechanic Changes in Passive Properties of Hemiplegic Ankles With Spastic Hypertonia", *Arch. Phys. Med. Rehabil.*, vol. 85:1638-1646 (2004).

* cited by examiner

*Primary Examiner* — Max Hindenburg
*Assistant Examiner* — Charles Becker
(74) *Attorney, Agent, or Firm* — Fish & Richardson P.C.

(57) ABSTRACT

A measurement device (10) for quantitatively measuring stiffness, torque or range of motion (ROM) around the joint axis of the ankle-foot complex of a lower limb in the sagittal and coronal planes, the device (10) comprising: a plate (13, 21) for placement of the ankle-foot complex, the plate (13, 21) operatively connected to an actuator (14, 16) for manual actuation; an angular measurement device (12, 17) to measure an angular position of the ankle-foot complex; a torquemeter (11) to measure resistance torque of the ankle-foot complex; an electromyograph (48) to monitor muscular activity of muscles of the lower limb; and computer software to record the measured angular position, resistance torque of the ankle-foot complex and EMG of the lower limb muscles.

17 Claims, 17 Drawing Sheets

ANKLE-FOOT ORTHOSIS PRESCRIPTION ASSISTIVE DEVICE

TECHNICAL FIELD

The invention relates to a measurement device for quantitatively measuring stiffness, torque or range of motion (ROM) of an ankle joint or an ankle-foot orthosis (AFO) in the sagittal and coronal planes of the ankle-foot complex. In particular, the invention assists a prescription of an AFO for persons with a spastic or flaccid ankle joint.

BACKGROUND

AFOs are commonly prescribed as a form of orthotic intervention to improve gait of patients with neuromuscular diseases, such as stroke, cerebral palsy or brain injury. They are primarily designed to provide adequate plantarflexion resistance, to prevent foot-drop and to provide sufficient medio-lateral stability for a pathologic ankle joint. Therefore, quantitative information on stiffness of an ankle joint and an AFO in the sagittal and coronal planes is essential in an AFO prescription.

An understanding of stiffness properties inherent in the design of an AFO is important because it is the key in preventing an under- or over-prescription and in providing an optimum AFO for a patient. However, the complicated geometry of a thermoplastic AFO and its interaction with the lower limb make it difficult to evaluate the mechanical behavior of an AFO during gait. This has been one of the limitations for the development of a prescription system to provide the most appropriate AFO to patients with various medical conditions.

Spasticity is one of the most common neurological impairments and occurs after the lesion of the upper motor neuron (UMN) in patients with hemiplegia. It is defined as disordered sensori-motor control resulting from a UMN lesion and presenting as intermittent or sustained involuntary activation of muscles. Some studies indicate that about 36% to 38% of patients with stroke developed spasticity during the first year. Spasticity generally induces an increase in ankle joint stiffness and foot-drop during ambulation. Therefore, patients with a spastic ankle joint are prevalently prescribed with an AFO.

Joint stiffness is attributed to a reflex stiffness component which is caused by the alternation in the muscular activation level and a non-reflex stiffness component which stems from the mechanical properties of the muscles, joints and tendons. Both reflex and non-reflex changes occur at an ankle joint in patients with hemiplegia.

A clinician usually evaluates ankle joint stiffness of a patient manually and attempts to reflect its input for decision making in the design of an AFO. However, this protocol heavily relies on the anecdotal or individual clinical experience. In the laboratory setting, a number of sophisticated experimental devices have been introduced to assess resistive torque and stiffness of a spastic ankle joint, such as a device disclosed in U.S. Pat. No. 6,599,255 B2. However, these devices might not be very practical in the clinical setting due to their size, costs and complexity.

In a clinical environment, a manual device is more practical. They can minimize discomfort and injuries and are considered safer than automated devices and easily applied in a clinical environment. However, they have the disadvantage that the applied force, velocity, and acceleration achieved as well as the point of force application and their orientation are difficult to control.

Traditionally, it is believed that stiffness of an ankle joint and an AFO should be considered in an AFO prescription. There is no available device to perform this function. Accordingly, there is a need for a manual device which can measure stiffness of both an ankle joint and an AFO quantitatively in order to assist a clinician in an AFO prescription. It would be beneficial for a patient if a clinician is able to prescribe an AFO based on the objective information on stiffness of an ankle joint and an AFO instead of a subjective decision that may be based on their experience.

SUMMARY

In a first aspect, there is provided a measurement device for quantitatively measuring stiffness, torque or range of motion (ROM) around the joint axis of the ankle-foot complex of a lower limb in the sagittal and coronal planes, the device comprising: a plate for placement of the ankle-foot complex, the plate operatively connected to an actuator for manual actuation; an angular measurement device to measure an angular position of the ankle-foot complex; a torquemeter to measure resistance torque of the ankle-foot complex; an electromyograph (EMG) to monitor muscular activity of muscles of the lower limb; and computer software to record the measured angular position, resistance torque of the ankle-foot complex and EMG of the lower limb muscles.

The plate may be a foot plate or a rotary plate.

The angular measurement device may be a potentiometer or a protractor.

The foot plate may have range of motion in the sagittal and coronal planes, and range of motion of the foot plate is adjustable with stoppers positioned under a handle.

The device may further comprise a base and base frames to support the device, wherein the angular position of the base relative to the base frame is adjustable in the sagittal plane.

The device may further comprise a metronome to monitor angular velocity of the foot plate.

The device may further comprise a rotary plate to fix the ankle-foot complex via the foot plate, the foot plate being freely movable on the rotary plate and its height is adjustable to enable correct positioning of the axis of the rotary plate to the estimated rotational center of the ankle-foot complex with reference to the extended axis of the torquemeter and the potentiometer.

The actuator may be a handle or a steering wheel to manually rotate the rotary plate around the axis of the torquemeter and the potentiometer.

The EMG may comprise electrodes attached to dorsiflexor and plantarflexor muscles.

The device may further comprise a hand-held dynamometer and associated software to measure muscle strength of each joint to determine an AFO prescription.

Optimum stiffness of an AFO ($K_{AFO}$) may be determined considering strength of the lower limb joint.

Range of motion of the ankle joint may be measured by the device to determine an AFO prescription.

Range of motion of an ankle joint ($ROM_{ANKLE}$) and range of motion of an AFO ($ROM_{AFO}$), $ROM_{ANKLE} \geq ROM_{AFO}$ may be satisfied.

Range of motion of an ankle joint ($ROM_{ANKLE}$) or an AFO ($ROM_{AFO}$) may be measured using the device in the sagittal and coronal planes.

Range of motion of an ankle joint may be measured by quantifying the ankle-foot complex angular position that reaches predetermined torque values in both directions in the plane of interest, and range of motion of the ankle is the summation of absolute angular position values in both directions.

Range of motion of an ankle joint may be measured by stretching the ankle-foot complex to its limit in both directions in the plane of interest and quantify their values, and range of motion of the ankle is the summation of absolute angular position values in both directions.

In a second aspect, there is provided a method for quantitatively measuring stiffness of an ankle joint and an AFO, the method comprising: using the equation $K=\Delta T/\Delta\theta$; wherein K is stiffness and $\Delta T$ is torque increments during a certain amount of ankle-foot complex angular movement ($\Delta\theta$).

Stiffness ($K_{ANKLE}$) data of an ankle joint and an AFO may be used to determine whether optimum stiffness of a prescribing AFO ($K_{AFO}$), and $K_{AFO} \geq K_{ANKLE}$ may be satisfied.

Resistance torque ($T_{ANKLE}$) data of an ankle joint and an AFO may be used to determine whether optimum resistance torque of a prescribing AFO ($T_{AFO}$) at a predetermined ankle-foot complex angular position, and $T_{AFO} \geq T_{ANKLE}$ may be satisfied.

In a third aspect, there is provided a method for controlling angular velocity of a foot plate and a rotary plate of a measurement device for quantitatively measuring stiffness, torque or range of motion (ROM) around the joint axis of the ankle-foot complex of a lower limb in the sagittal and coronal planes, the method comprising: using the equation $Av=(Mt*Rm)/60$; wherein Av is angular velocity, Mt is motional tempo, and Rm is range of motion of an ankle joint ($ROM_{ANKLE}$) or an AFO ($ROM_{AFO}$).

The angular velocity may be monitored by a metronome.

DESCRIPTION OF DRAWINGS

An example will now be described with reference to the accompanying drawings, in which.

DETAILED DESCRIPTION

Figure 1:
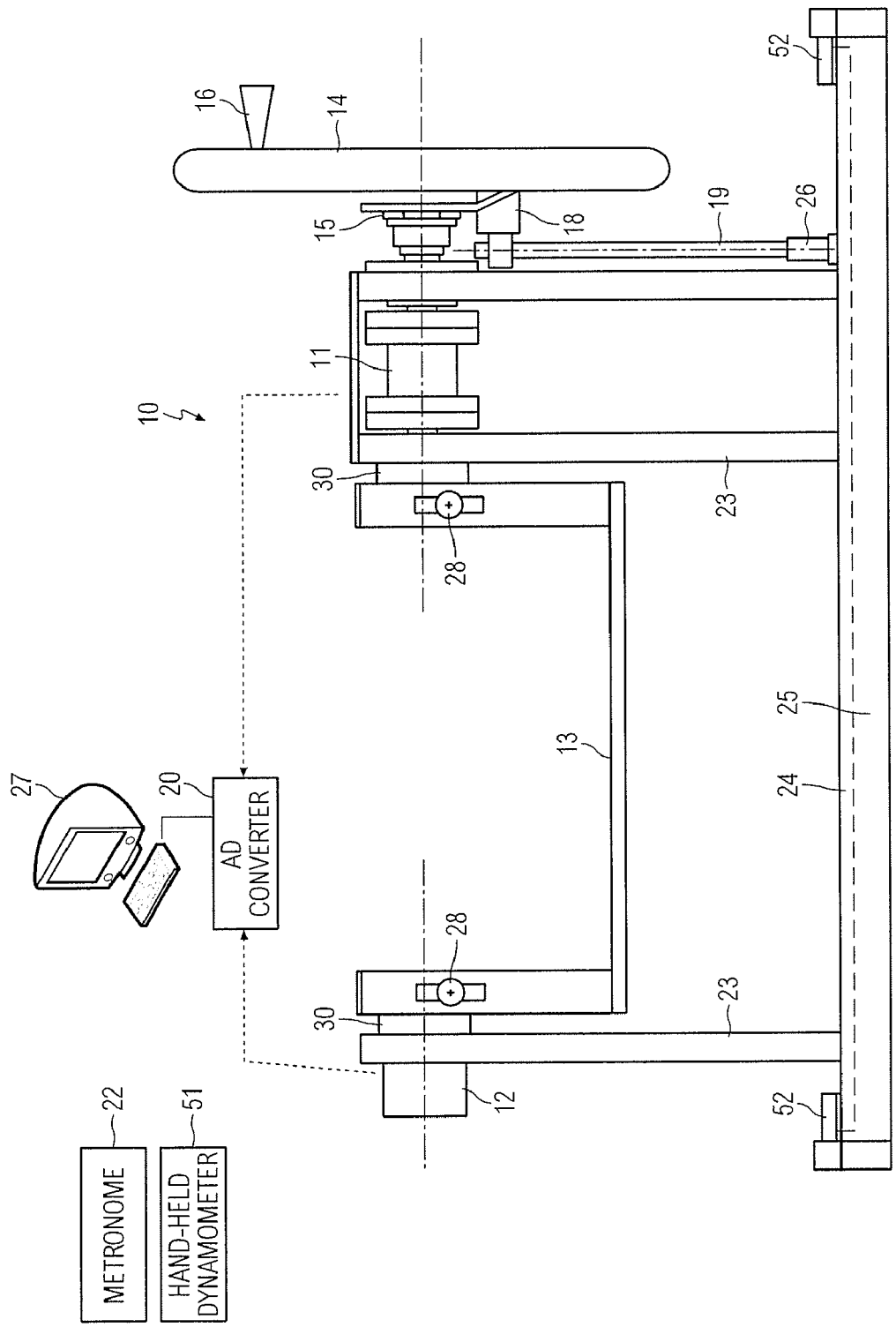
FIG. 1 is a front view of the body of a device to measure stiffness, torque or range of motion (ROM) around the joint axis of the ankle-foot complex according to an embodiment of the present invention.
Figure 2:
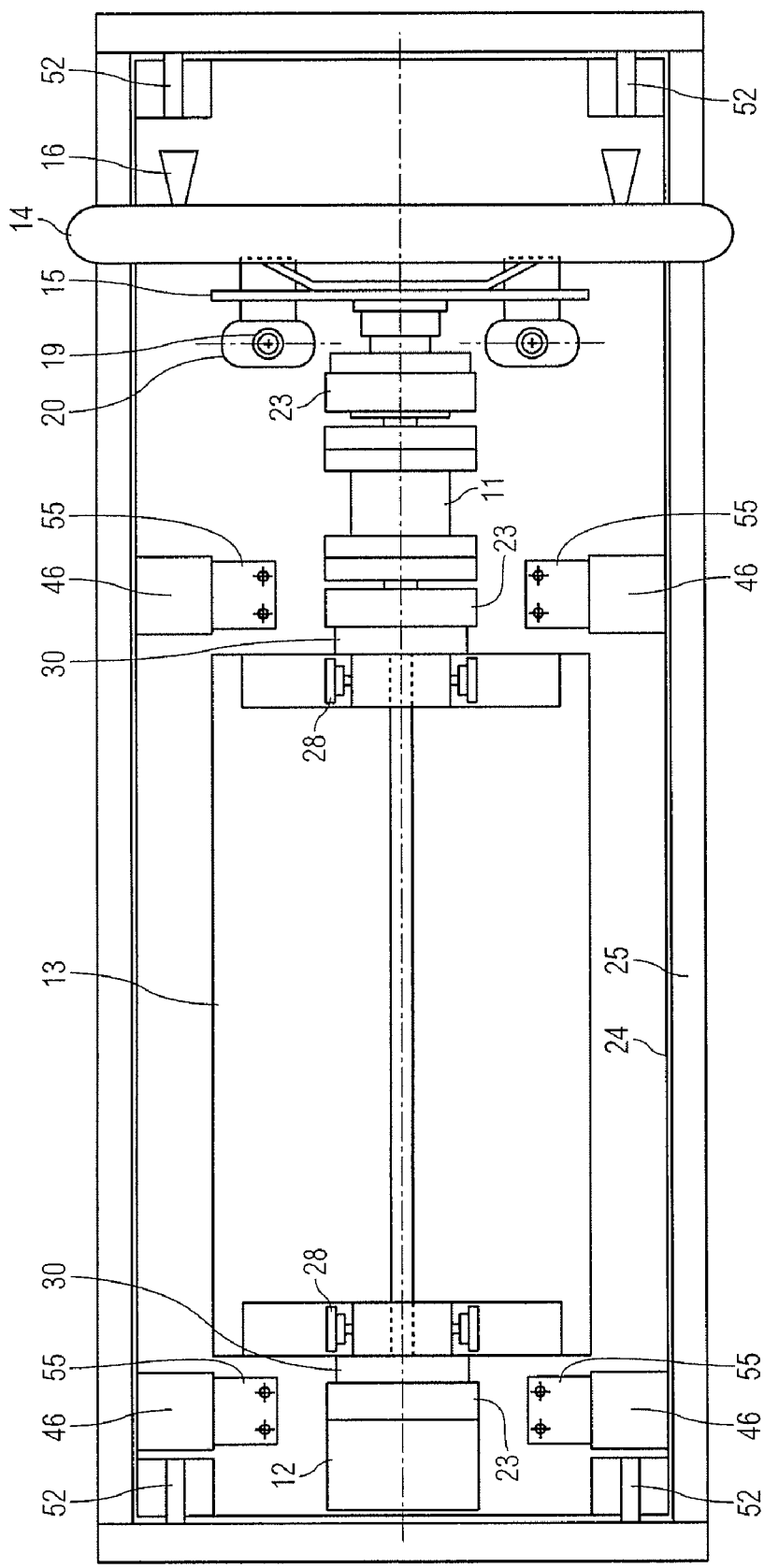
FIG. 2 is a transverse view of the body of the device of FIG. 1.
Figure 3:
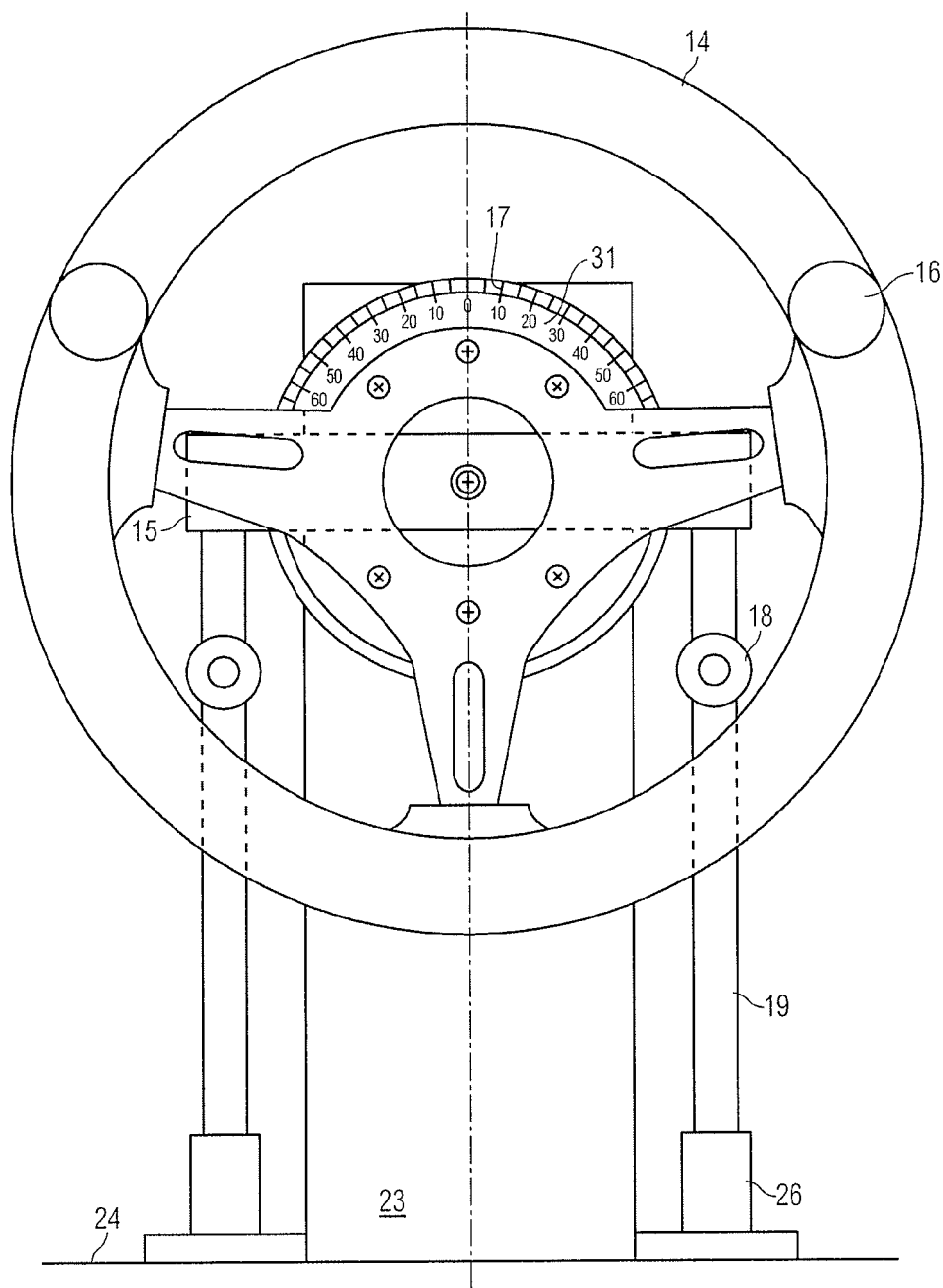
FIG. 3 is a sagittal view of the body of the device of FIG. 1 from the steering wheel.

Referring to FIGS. 1 to 3, an ankle-foot orthosis prescription assistive device 10 is provided. The device 10 quantitatively measures stiffness, torque or range of motion (ROM) of an ankle joint or an ankle-foot orthosis (AFO) in the sagittal and coronal planes of the ankle-foot complex. The body of the device 10 generally a torquemeter 11, a potentiometer 12, a rotary plate 13, a steering wheel 14 with a stopper bar 15 and a handle 16, a protractor 17, and a urethane stopper 18. The height position of the urethane stopper 18 is adjustable along a stopper pole 19. The device 10 is able to measure angular positions with the potentiometer 12 and their corresponding resistance torque with the torquemeter 11 around the rotational center of the ankle joint and the AFO in the sagittal and coronal planes by applying manual force to the steering wheel 14 or the handle 16, which extends a shaft in a lateral direction to the rotary plate 13. The full scale of the torquemeter 11 is 50 Nm. Output from the torquemeter 11 and the potentiometer 12 is fed into a computer 27 via an A/D converter 20 for further analysis. Range of motion (ROM) of a foot plate 21 is adjustable with the urethane stoppers 18 positioned under the stopper bar 15 attached to the steering wheel 14.

The protractor 17 is used to provide visual information of the angular positions of the ankle joint or the AFO in the sagittal and coronal planes of the ankle-foot complex to an examiner during assessment. The angular velocity of the foot plate 21 is monitored with a metronome 22.

The handle 16 is attached to the steering wheel 14. The steering wheel 14, the torquemeter 11 and the potentiometer 12 are held by supporters 23 standing on a base 24 of the device 10. The torquemeter 11 measures resistance torque, while the potentiometer 12 measures the angular position. The output from the torquemeter 11 and the potentiometer 12 are fed into the computer 27 for further analysis via an A/D converter 20. Spacers 30 are positioned between the supporters 23 and the rotary plate 13 to reduce friction between them. The base 24 is fixed above base frames 25 of the device 10 using the base holder 52. A supporting frame holder 55 on the base 24 of the device 10 is used to maintain a supporting frame 46 to fixate a lower limb or an AFO. Manual force is applied to either the handle 16 or the steering wheel 14 to rotate the rotary plate 13 around the axis of the potentiometer 12 and the torquemeter 11. The height of a rotary plate 13 is adjustable and fixed to a desired location using nut screws 28. The stopper bar 15 fixed to the steering wheel 14 moves around with it. A urethane stopper 18 whose height is adjustable along a stopper pole 19 is utilized to restrict ROM of the rotary plate 13 and the foot plate for safety reasons and controlling the applied angular velocity using the metronome 22. The stopper pole 19 is fixed to the base 24 of the device 10 with a stopper pole stand 26. The protractor 17 is fixed around the rotational axis and it can provide visual information of the rotational angle. This is possible by placing a circular transparent plastic sheet 31 with an arrow, which rotates along with the steering wheel 14 over the fixed protractor 17.

Figure 4:
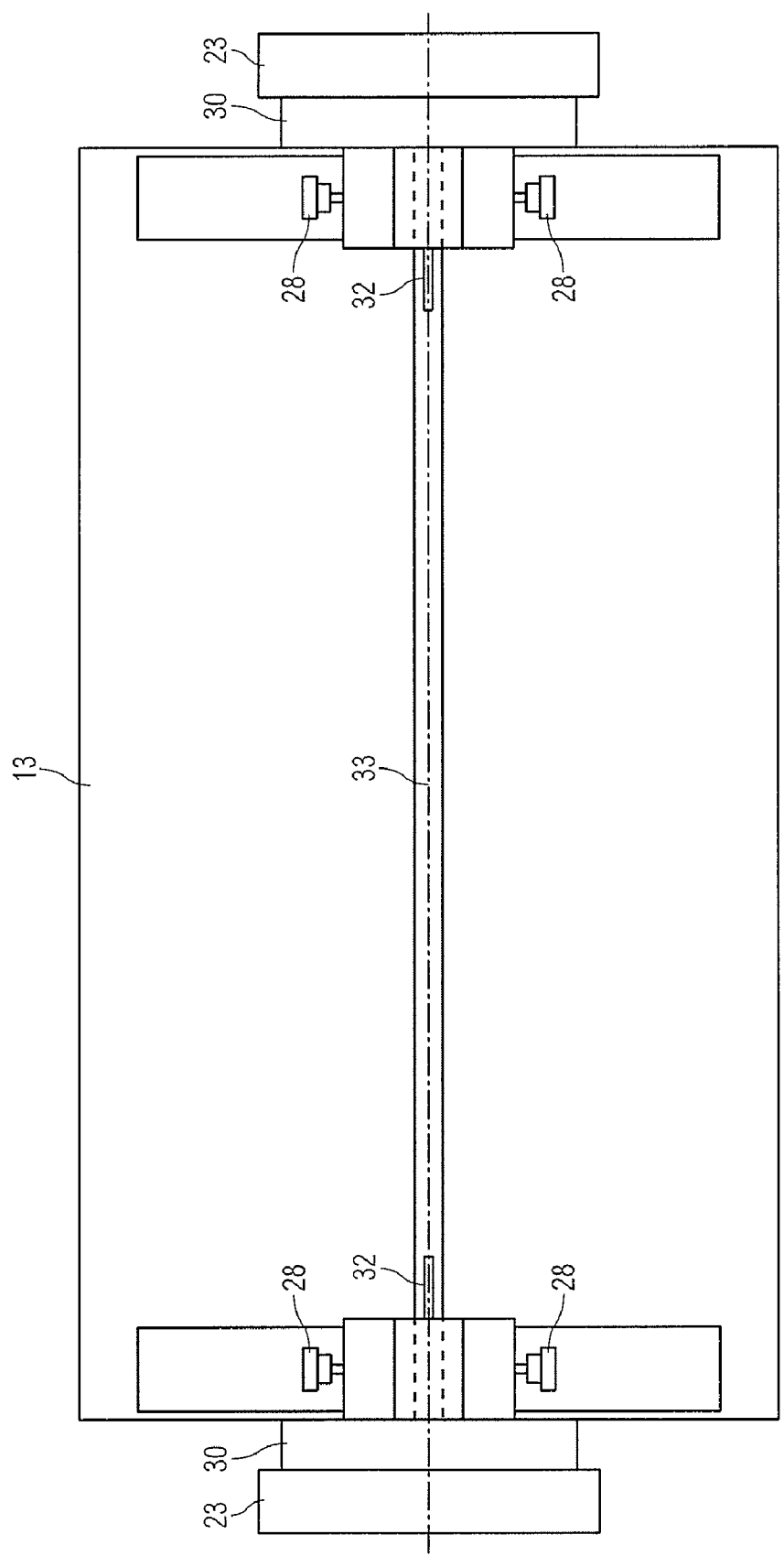
FIG. 4 is a transverse view of the rotary plate and its fixation to the supporter of the device of FIG. 1.
Figure 5:
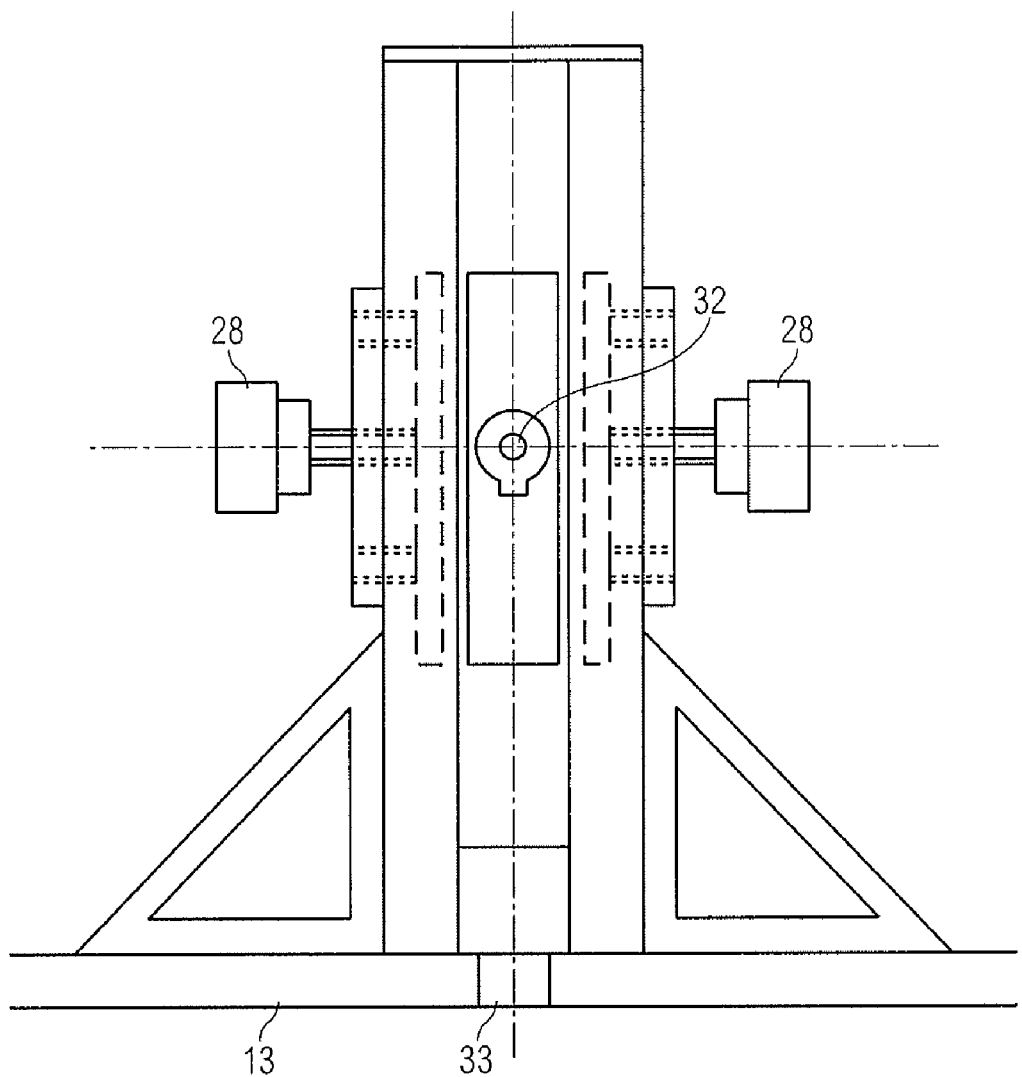
FIG. 5 is a sagittal view of the rotary plate of FIG. 4.

Referring to FIGS. 4 and 5, the rotary plate 13 comprises two separate plates and has a groove 33 between them. The groove 33 is used to position a foot plate 21 at an appropriate location on the rotary plate 13. A screw 32 is provided which protrudes from the rotational axis of the torquemeter 11 and the potentiometer 12 to extend a horizontal line, so that it can visually assist in locating the rotational center of an ankle joint and an AFO. Spacers 30 are positioned between the supporter 23 of the device 10 and the rotary plate 13 to reduce friction between them.

Figure 6:
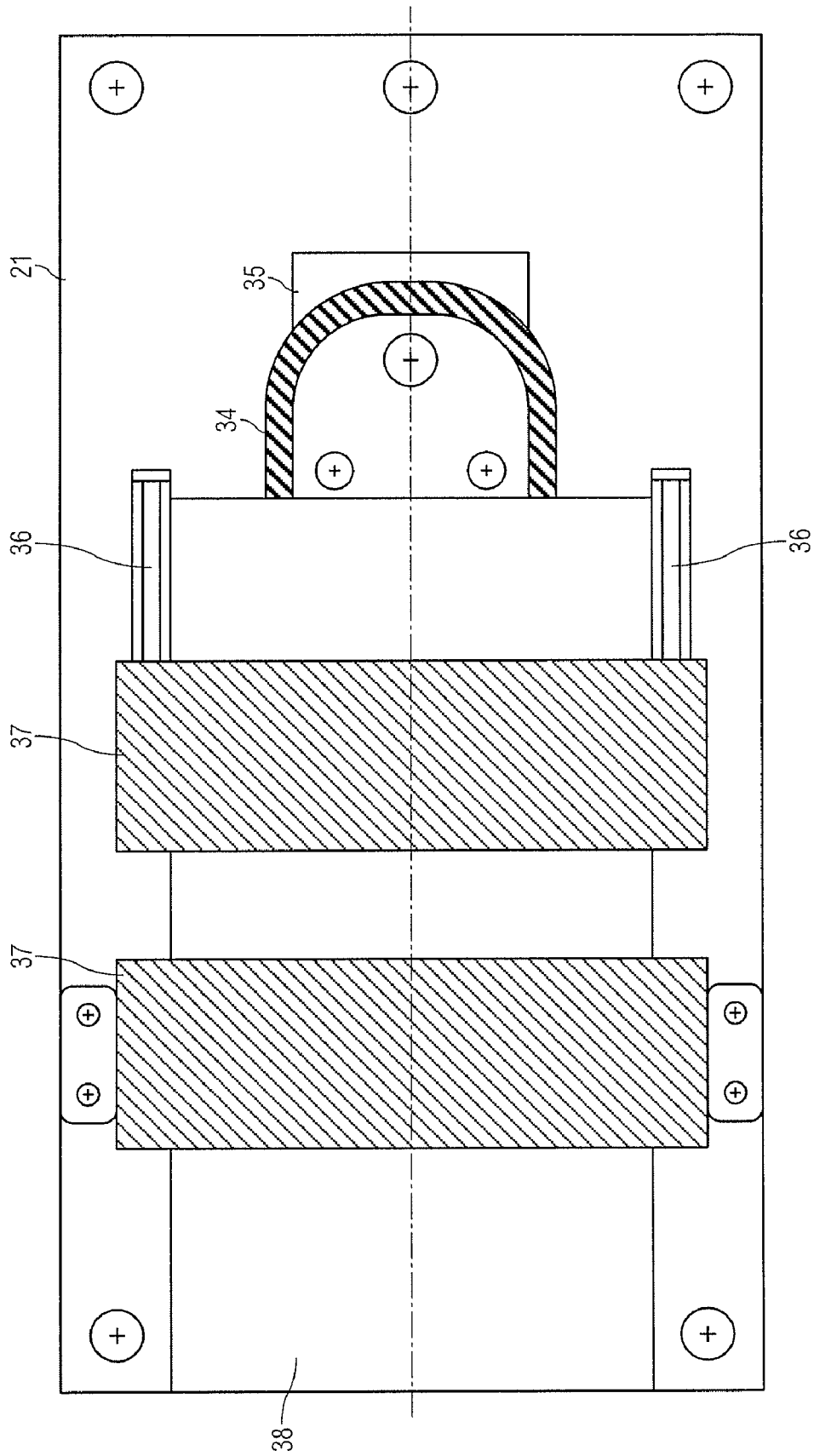
FIG. 6 is a front side of the foot plate for sagittal plane measurement of the ankle-foot complex.
Figure 7:
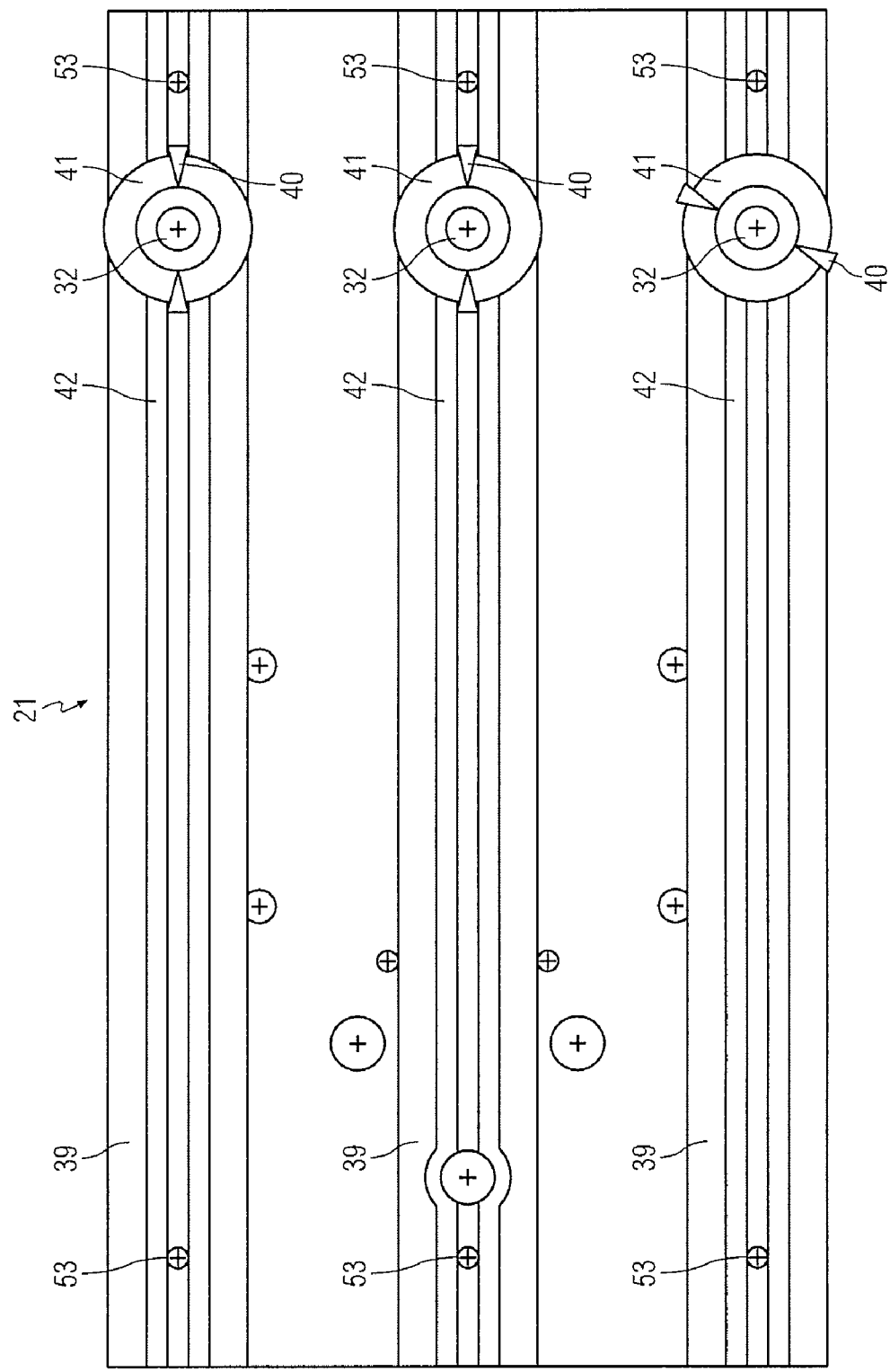
FIG. 7 is a back side of the foot plate for sagittal plane measurement of the ankle-foot complex.

FIG. 6 is a front side of the foot plate 21 and FIG. 7 is a back side of the foot plate 21 for sagittal plane measurement of an ankle joint. A heel cup 34 is positioned on a metal plate 35, which allows a convenient replacement of various heel cups 34 according to a foot size. Velcro™ straps 37 are used to fix the ankle-foot complex to the foot plate 21. The position of one strap 37 is adjustable along a strap holder 36, while the other strap 37 is fixed. A rubber sheet 38 is sealed on the foot plate 21 as a slip stopper. Three metal frames each with a groove 42 are embedded in a parallel manner at the back of the foot plate 21. The head of the screw 32 fits in the groove 42 of the metal frames 39 and the screws 32 are used to fix the foot plate 21 to the rotary plate 13. The head of the screw 32 can move freely along the grooves 42 of the metal frames 39 between the stoppers 53 and their positions are fixed by fly nuts 40 and washers 41 on the rotary plate 13.

Figure 8:
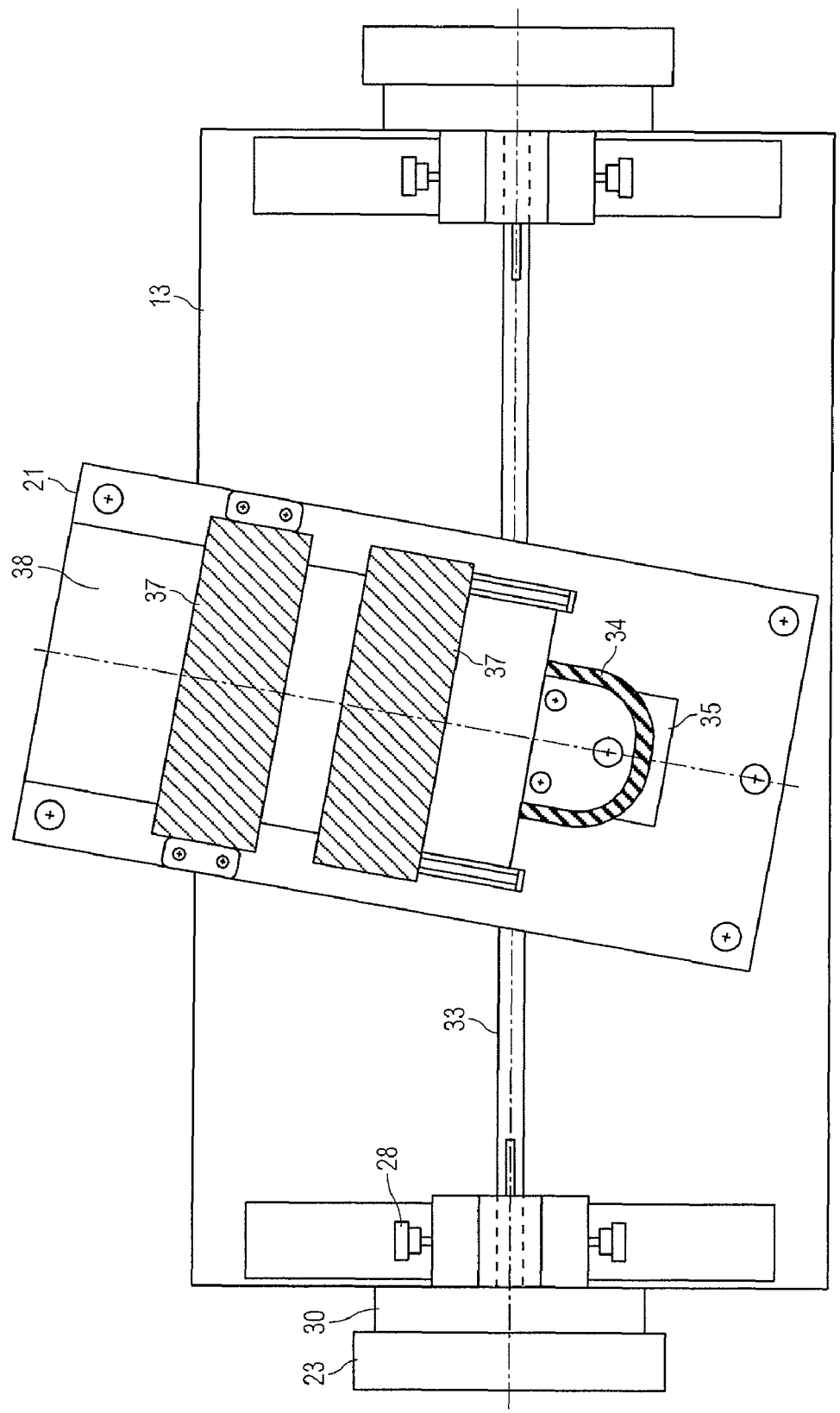
FIG. 8 is a foot plate attached to a rotary plate for sagittal plane measurement of the ankle-foot complex.

FIG. 8 illustrates the foot plate 21 attached to the rotary plate 13 for sagittal plane measurement of the ankle joint. The screws 32 extruding from the metal frames 39 at the back of the foot plate 21 are fit into the groove 33 of the rotary plate 13. Subsequently, the position of the foot plate 21 on the rotary plate 13 is fixed by tightening the fly nuts 40 over the washers 41.

Figure 9:
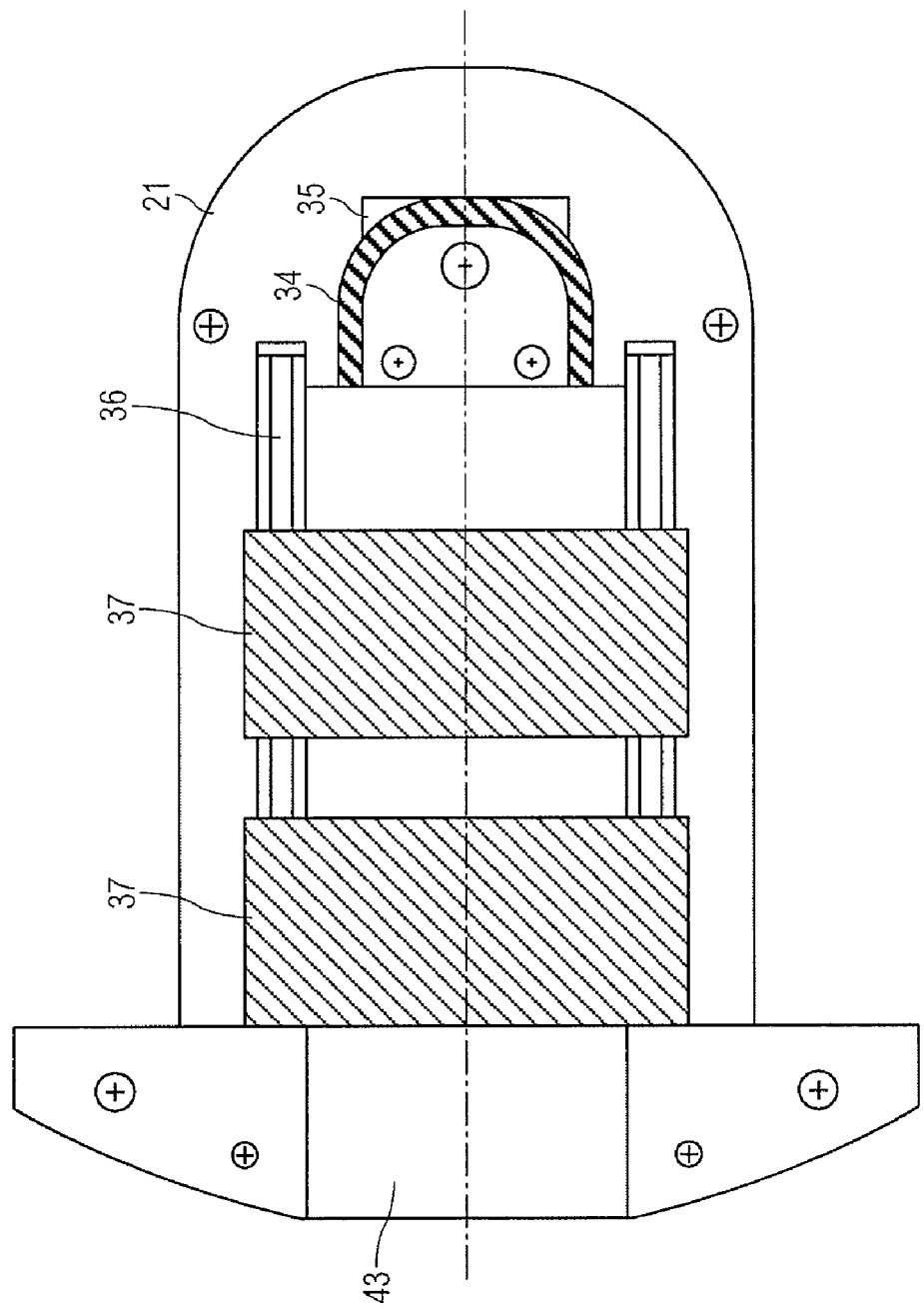
FIG. 9 is a front side of the foot plate for coronal plane measurement of the ankle-foot complex.
Figure 10:
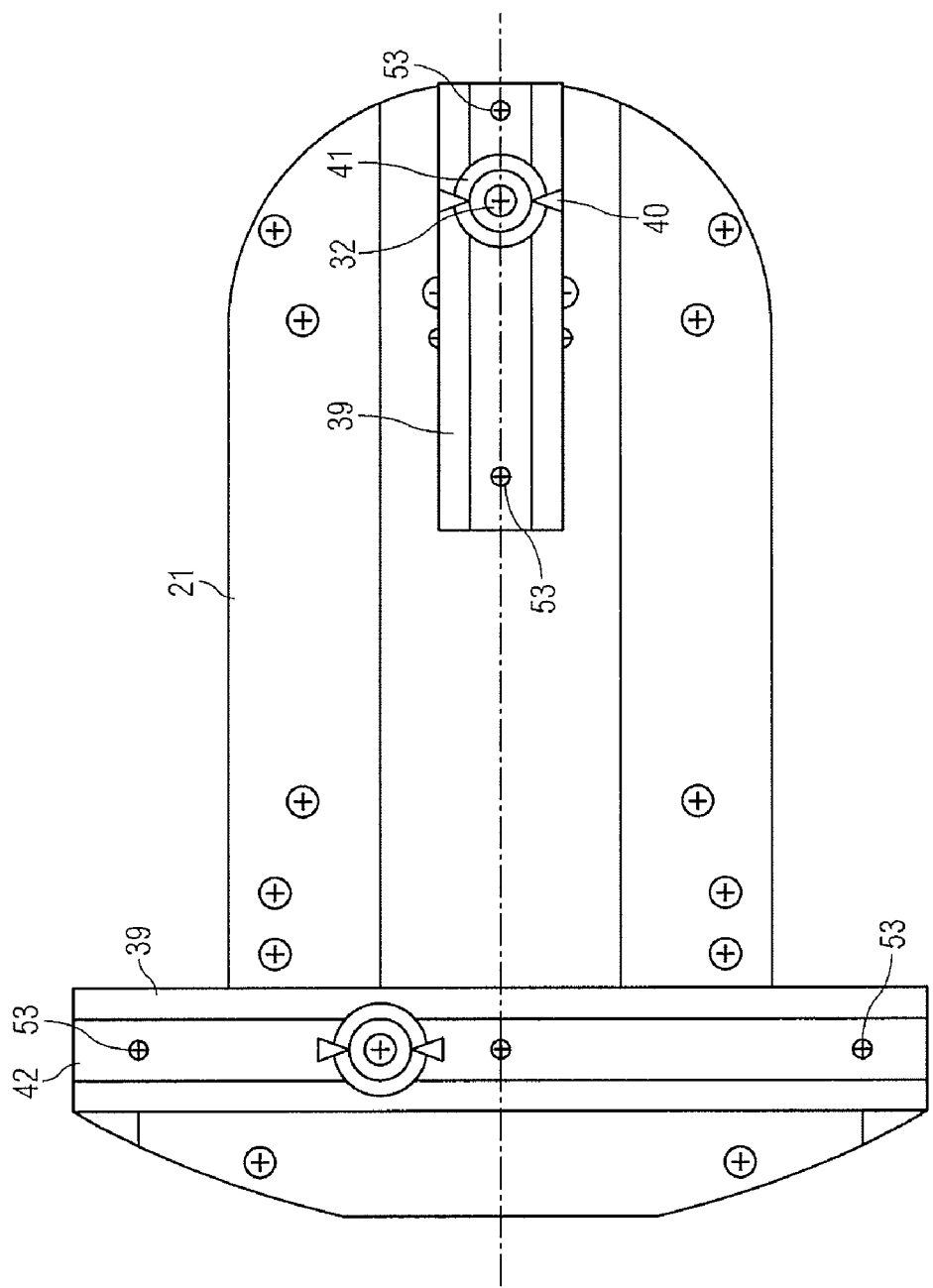
FIG. 10 is a back side of the foot plate for coronal plane measurement of the ankle-foot complex.

FIG. 9 is a front side of the foot plate 21 and FIG. 10 is a back side of the foot plate 21 for coronal plane measurement of an ankle joint. The heel cup 34 is positioned on the metal plate 35, which allows a convenient replacement of various heel cups 34 according to a foot size. Straps 37 are used to fix the ankle-foot complex to the foot plate 21. The position of the straps 37 is adjustable along a strap holder 36. A rubber sheet 43 is sealed on the foot plate 21 as a slip stopper.

Figure 11:
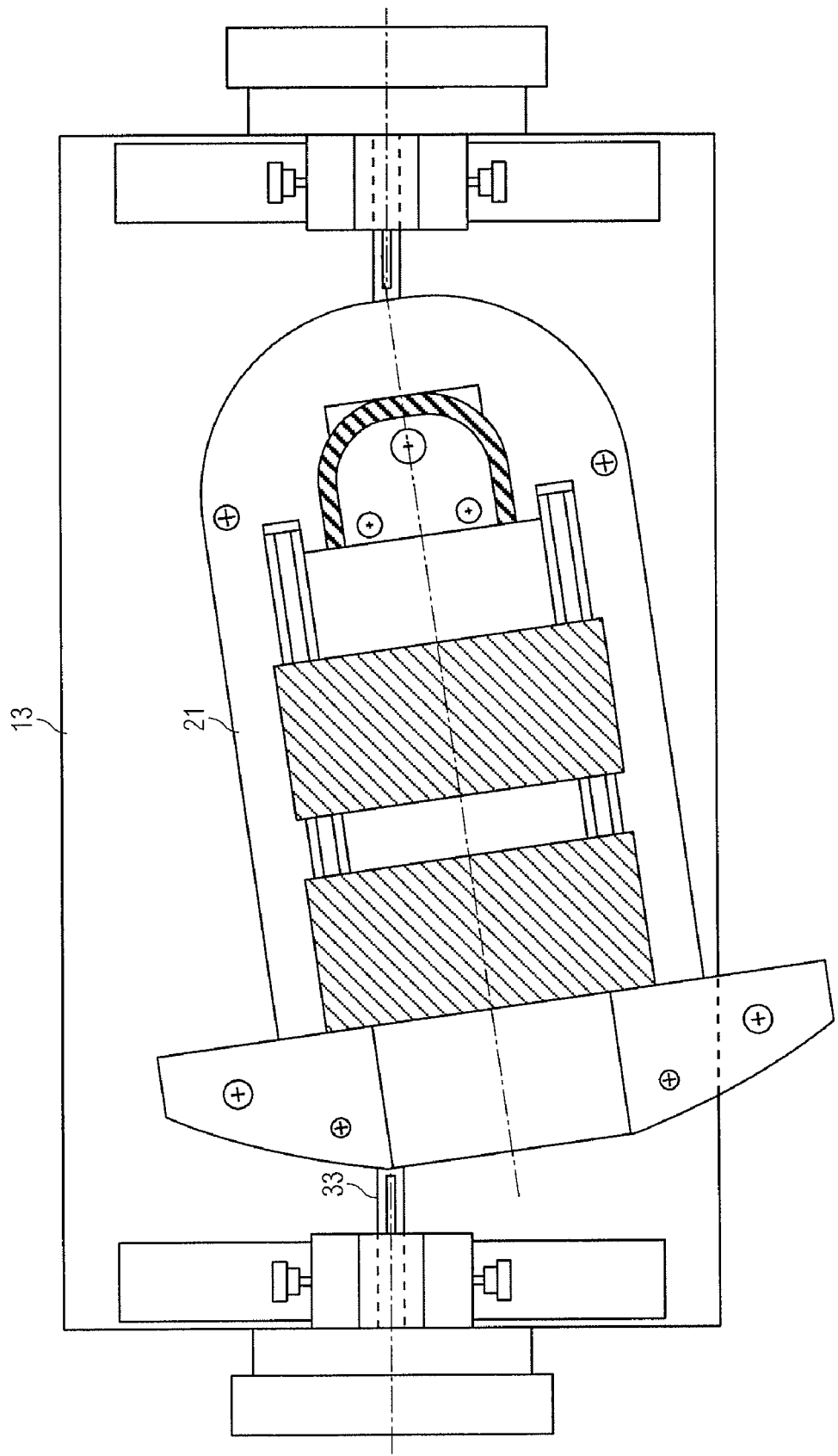
FIG. 11 is a foot plate attached to a rotary plate for coronal plane measurement of the ankle-foot complex.

The two metal frames 39 with a groove 42 are embedded at a right angle at the back of the foot plate 21. The head of the screw 32 fits in the groove 42 of the metal frames 39 to fix the foot plate 21 to the rotary plate 13. The head of the screws 32 can move freely along the groove 42 of the metal frames 39 between the stoppers 53 and their positions are fixed by the fly nuts 40 and washers 41. FIG. 11 depicts the foot plate 21 attached to the rotary plate 13 for coronal plane measurement of the ankle joint. The head of the screws 32 extending from the metal frames 39 of the foot plate 21 are fit into the groove 33 of the rotary plate 13. Subsequently, the position of the foot plate 21 on the rotary plate 13 is fixed by tightening the fly nuts 40 over the washers 41.

Figure 12:
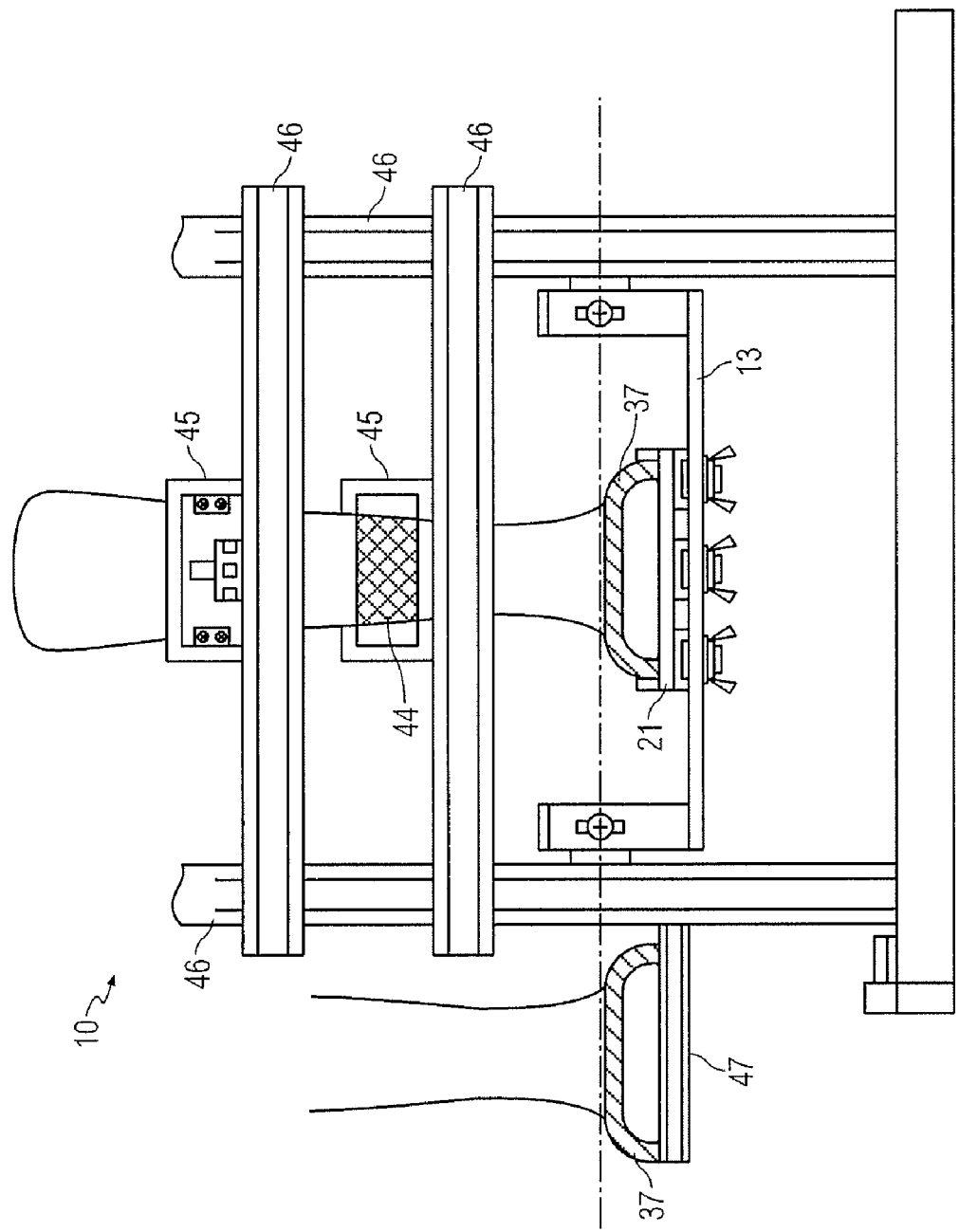
FIG. 12 is a front view of a limb and a device to measure stiffness, torque or range of motion of an ankle joint in the sagittal plane in accordance with an embodiment of the present invention.
Figure 13:
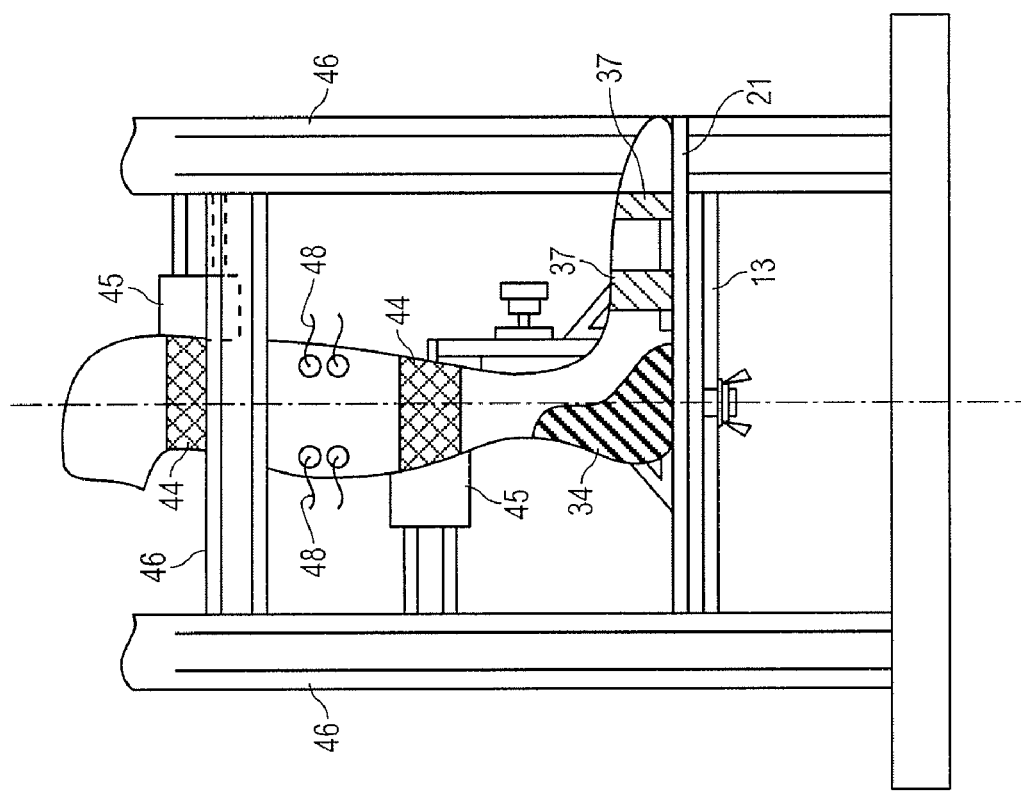
FIG. 13 is a sagittal view of a limb and a device to measure stiffness, torque or range of motion of an ankle joint in the sagittal plane in accordance with an embodiment of the present invention.

Referring to FIGS. 12 and 13, a limb and the device 10 to measure stiffness, torque or range of motion of an ankle joint in the sagittal plane is provided. The ankle-foot complex is fastened to the foot plate 21 by straps 37 of the foot plate 21, while a shank of a lower-limb is fastened by a strap 44 extending from a padding 45, which is fixed to the supporting frames 46 maintained by the supporting frame holders 55 on the base 24 of the device 10. The contra-lateral ankle-foot complex is placed on a foot rest 47. While stretching the ankle joint of interest, ankle joint torque ($T_{ANKLE}$), its corresponding angular positions and electromyographic signals from the dorsiflexor and plantarflexor muscles of the lower limb are recorded by an electromyograph (EMG). The EMG signals are collected using electrodes 48 attached to theses muscles. Signals from the torquemeter 11, the potentiometer 12 and the EMG electrodes 48 are fed into the computer 27 via the A/D converter 20 for further analysis. Angular velocity of the rotation of the foot plate 21 is controlled and monitored using the metronome 22 utilizing the equation $Av=(Mt*Rm)/60$, wherein Av is angular velocity, Mt is motional tempo, and Rm is ROM of an ankle ($ROM_{ANKLE}$) or an AFO ($ROM_{AFO}$). ROM of an ankle ($ROM_{ANKLE}$) or an AFO ($ROM_{AFO}$) in the sagittal and coronal planes may be measured using the device 10. There are two methods to measure ROM. Firstly, ROM can be measured by quantifying the ankle-foot complex angular position that reaches predetermined torque values in both directions in the plane of interest. For instance, if the predetermined torque value is 5 Nm and its corresponding ankle angular position is 10° in dorsiflexion and 35° in plantarflexion in the sagittal plane, then ROM is their summation 45°. Secondly, ROM can be also measured by stretching the ankle-foot complex to its limit in both directions in the plane of interest and quantifying their values. For instance, if the limit position in the dorsiflexion direction is 15° and in the plantarflexion one is 40° in the sagittal plane, then ROM is their summation 55°.

Figure 14:
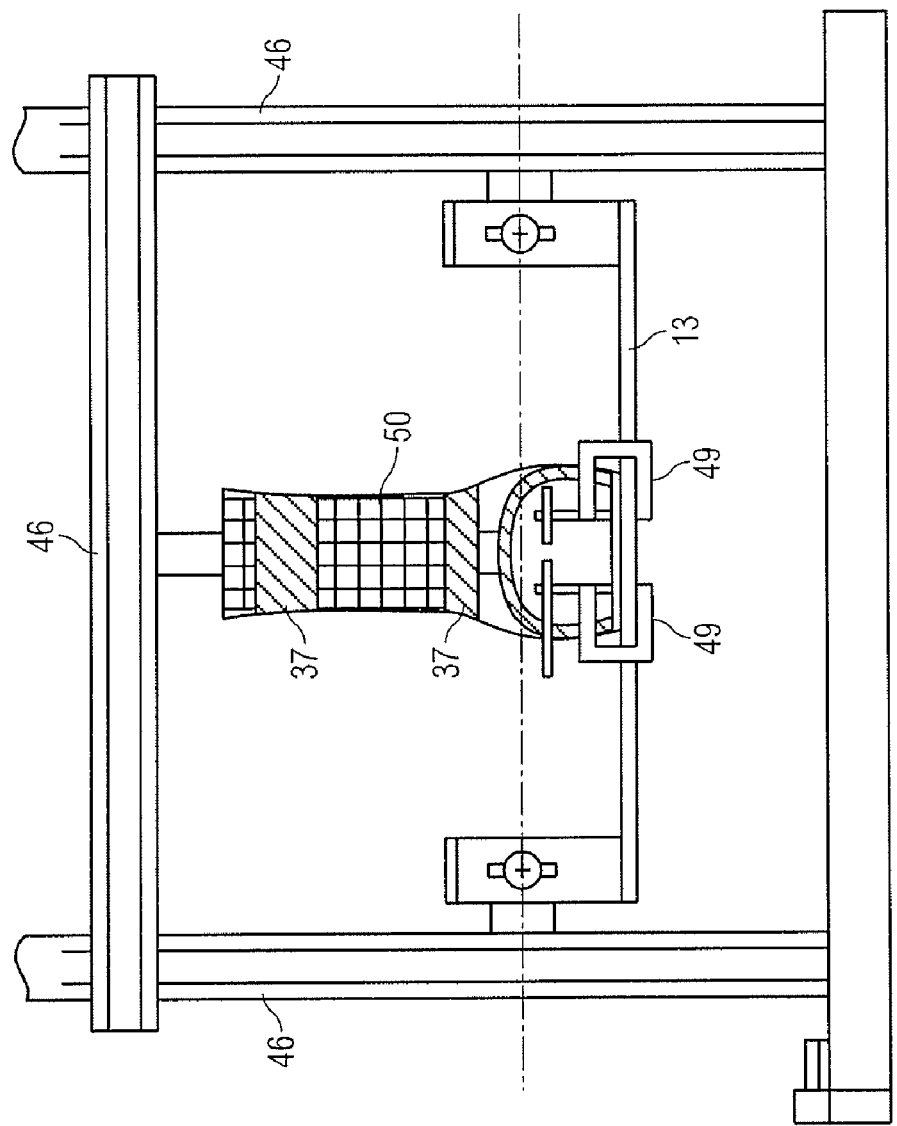
FIG. 14 is a front view of an AFO and a device to measure stiffness, torque or range of motion of an AFO in the sagittal plane in accordance with an embodiment of the present invention.
Figure 15:
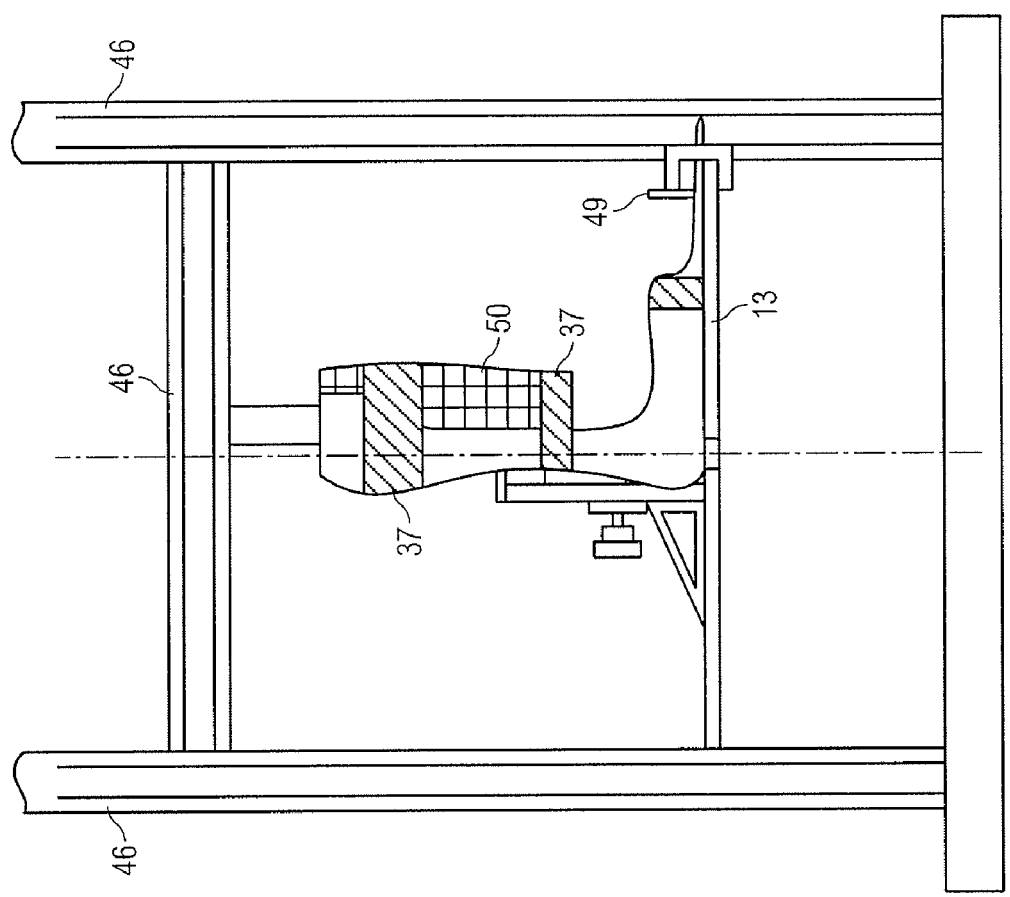
FIG. 15 is a sagittal view of an AFO and a device to measure stiffness, torque or range of motion of an AFO in the sagittal plane in accordance with an embodiment of the present invention.

Referring to FIGS. 14 and 15, an AFO and a device 10 to measure stiffness, torque or range of motion (ROM) of an AFO in the sagittal plane is provided. The AFO is fixed to the rotary plate 13 using a G-clamp 49. A shank of the AFO was fastened to the device using a dummy limb 50, which is fixed to the supporting frames 46 maintained by the supporting frame holders 55 on the base 24 of the device 10. While rotating the rotary plate 13, AFO torque ($T_{AFO}$) and its corresponding angle around the rotational axis are recorded. Signals from the torquemeter 11 and the potentiometer 12 are fed into the computer 27 via the A/D converter 20 for further analysis. Angular velocity of the rotation of the rotary plate 13 is controlled using the metronome 22 and ROM of the AFO ($ROM_{AFO}$) is measured as described above.

Stiffness of the ankle-foot complex is calculated using the equation $K=\Delta T/AO$, where K is stiffness and $\Delta T$ is torque increments during a certain amount of ankle angular movement ($\Delta\theta$). $\Delta\theta$ is determined based on ROM of the ankle joint ($ROM_{ANKLE}$) or the AFO ($ROM_{AFO}$).

Optimum stiffness of an AFO ($K_{AFO}$) is determined based on stiffness of an ankle joint ($K_{ANKLE}$). In order to keep the ankle joint at a desired angular position with effective plantarflexion resistance of an AFO, the following equation is satisfied: $K_{AFO} \geq K_{ANKLE}$.

Figure 16:
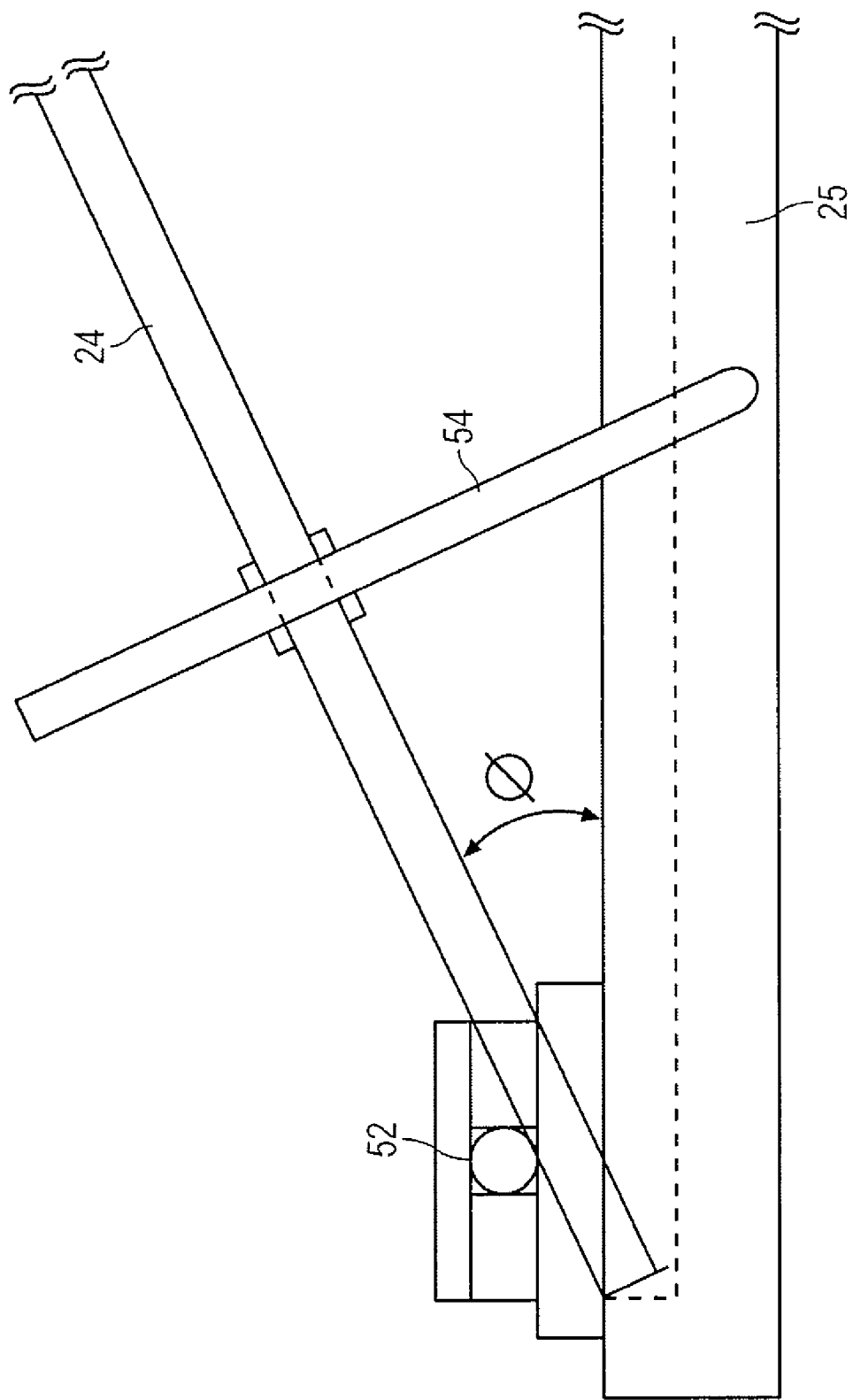
FIG. 16 is a sagittal view of the device of FIG. 1 showing a mechanism to alter the angular position of the base relative to the base frame.

Referring to FIG. 16, the angular position ($\Phi$) of the base 24 relative to the base frame 25 is adjustable by rotating the base 24 around the base holder 52 and maintain this angular position utilizing the angle adjuster 54. The ability to adjust and maintain the angular position is advantageous when a measurement of ankle joint stiffness, torque or range of motion is required to be conducted at various knee joint angular positions or postures.

Figure 17:
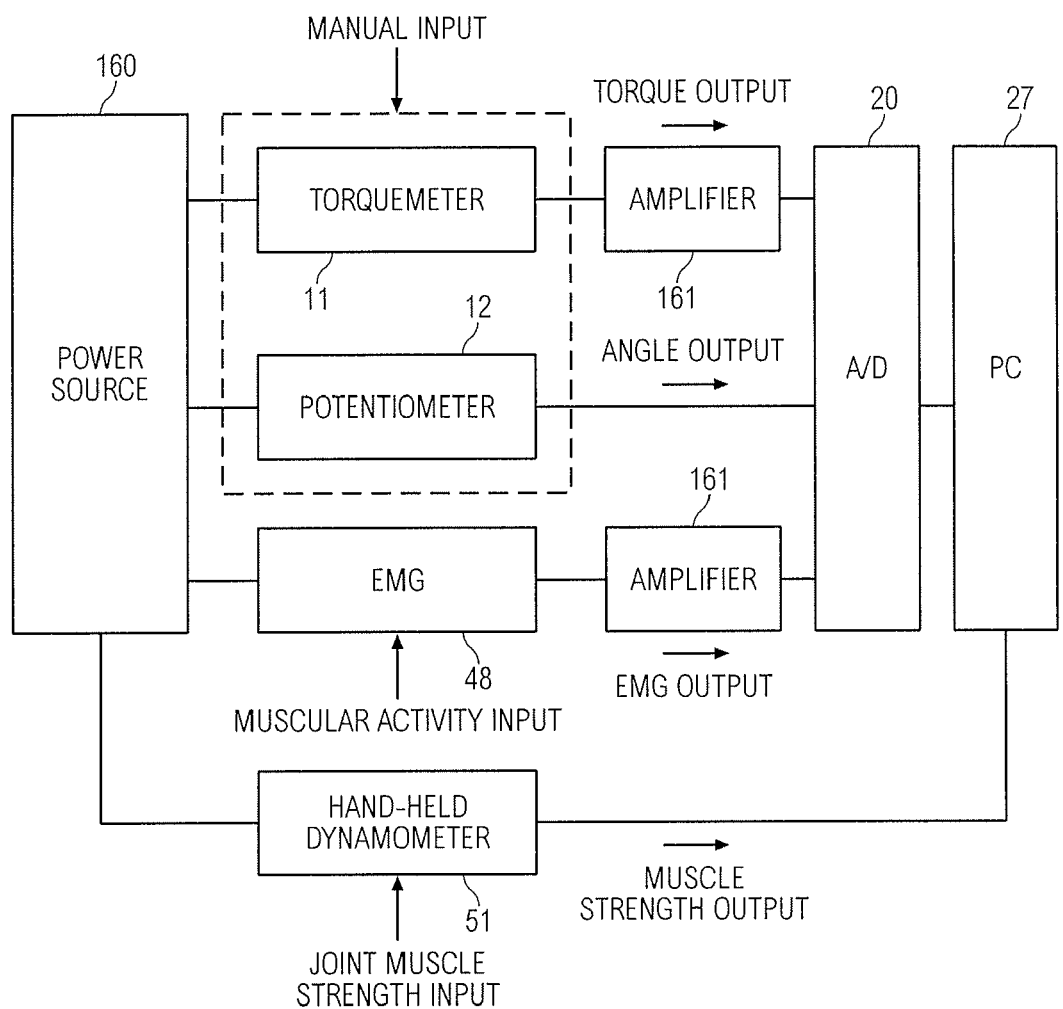
FIG. 17 is an electronic design diagram of the device of FIG. 1 with a hand-held dynamometer.

Referring to FIG. 17, an electronic design of the device 10 is illustrated. A power source 160 supplies appropriate voltage to the torquemeter 11, the potentiometer 12, the EMG electrode 48, a hand-held dynamometer 51, and an amplifier 161. The output signal from the torquemeter 11 and the EMG electrode 48 is amplified with the amplifier 161 and fed into the computer 27 via the A/D converter 20. The output signal from the potentiometer 11 and the hand-held dynamometer 51 is directly fed into the computer 27 via the A/D converter 20. Computer software records the measured angular position, resistance torque of the ankle-foot complex and EMG signals of the lower limb muscles as well as muscle strength of the lower limb joints for further analysis. The hand-held dynamometer 51 is provided to measure muscle strength of the lower limb joints. The hand-held dynamometer 51 can measure strength of plantarflexors and dorsiflexors of ankle joints, and flexors and extensors of knee and hip joints. It is advantageous if muscle strength of each joint is considered in an AFO prescription along with stiffness, torque and range of motion data obtained from the device 10. It is beneficial to consider muscle strength because an AFO should be designed to compensate weaken lower limb muscle strength of patients with various medical conditions. Therefore, quantified muscle strength data would provide supplemental input for more reliable and evidence-based practice in an AFO prescription.

In another embodiment, range of motion of the ankle joint is measured by the device 10. A range of motion measurement is considered in an AFO prescription. Range of motion of the ankle joint should be considered together with stiffness, torque and muscle strength data. $ROM_{ANKLE} \geq ROM_{AFO}$ is satisfied. It is advantageous to consider ROM for an AFO prescription because stiffness of an AFO ($K_{AFO}$) and ROM of an AFO ($ROM_{AFO}$) are closely related to each other. Quantitative ROM data also helps a clinician to determine whether an articulated AFO (AAFO) or a non-articulated AFO (NAAFO) should be prescribed. $ROM_{AFO}$ should be considered in the design of both AAFOs and NAAFOs to optimize their function. Therefore, quantified ROM data would also provide supplemental input for more reliable and evidence-based practice in an AFO prescription.

Preferably, three components should be considered in the final prescription of an AFO:
1) Stiffness ($K_{AFO}$ and $K_{ANKLE}$) and/or torque ($T_{AFO}$ and $T_{ANKLE}$) data by the device 10;
2) ROM ($ROM_{AFO}$ and $ROM_{ANKLE}$) data by the device 10; and
3) Lower limb joints muscle strength data by the hand-held dynamometer 51.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

What is claimed is:

1. A measurement device for quantitatively measuring stiffness, torque or range of motion (ROM) around the joint axis of the ankle-foot complex of a lower limb of a seated subject in the sagittal and coronal planes, the device comprising:
   a plate for placement of the ankle-foot complex, the plate operatively connected to an actuator for manual actuation;
   an angular measurement device operatively connected to the plate to measure an angular position in the sagittal and coronal planes of the ankle-foot complex of the seated subject around the rotational center of the ankle-foot complex;
   a torquemeter operatively connected to the plate to measure resistance torque in the sagittal and coronal planes of the ankle-foot complex of the seated subject around the joint rotational center of the ankle-foot complex;
   an electromyograph (EMG) to monitor muscular activity of muscles of the lower limb; and
   computer software to record the measured angular position in the sagittal and coronal planes of the ankle-foot complex, the measured resistance torque in the sagittal and coronal planes of the ankle-foot complex, and the measured EMG of the muscles of the lower limb
   wherein the computer measures the stiffness, torque, or range of motion based on the measured angular position, the measured resistance torque, or the measured EMG.

2. The device according to claim 1, wherein the plate is a foot plate or a rotary plate.

3. The device according to claim 2, wherein the angular measurement device is a potentiometer or a protractor.

4. The device according to claim 2, wherein the foot plate has a range of motion in the sagittal and coronal planes, and the range of motion of the foot plate is adjustable with stoppers positioned under a handle.

5. The device according to claim 1, further comprising a base and base frames to support the device, wherein the angular position of the base relative to the base frame is adjustable in the sagittal plane.

6. The device according to claim 1, further comprising a metronome to monitor angular velocity of the foot plate.

7. The device according to claim 3, further comprising a rotary plate to fix the ankle-foot complex via the foot plate, the foot plate being freely movable on the rotary plate and its height is adjustable to enable correct positioning of the axis of the rotary plate to the estimated rotational center of the ankle-foot complex with reference to the extended axis of the torquemeter and the potentiometer.

8. The device according to claim 7, wherein the actuator is a handle or a steering wheel to manually rotate the rotary plate around the axis of the torquemeter and the potentiometer.

9. The device according to claim 1, wherein the EMG comprises electrodes attached to dorsiflexor and plantarflexor muscles.

10. The device according to claim 1, further comprising a hand-held dynamometer and associated software to measure muscle strength of each joint to determine an ankle-foot orthosis (AFO) prescription.

11. The device according to claim 10, wherein optimum stiffness of an AFO ($K_{AFO}$) is determined considering strength of the lower limb joint.

12. The device according to claim 10, wherein the range of motion of an ankle joint is measured by the device to determine an AFO prescription.

13. The device according to claim 12, wherein the range of motion of an ankle joint ($ROM_{ANKLE}$) and the range of motion of an AFO ($ROM_{AFO}$), $ROM_{ANKLE} > ROM_{AFO}$ is satisfied.

14. The device according to claim 13, wherein the range of motion of an ankle joint ($ROM_{ANKLE}$) or an AFO ($ROM_{AFO}$) is measured using the device in the sagittal and coronal planes.

15. The device according to claim 14, wherein the range of motion of an ankle joint is measured by quantifying the ankle-foot complex angular position that reaches predetermined torque values in both directions in the plane of interest, and the range of motion of the ankle is the summation of absolute angular position values in both directions.

16. The device according to claim 14, wherein the range of motion of an ankle joint is measured by stretching the ankle-foot complex to the limit of the ankle joint in both directions in the plane of interest and quantify their values, and the range of motion of the ankle is the summation of absolute angular position values in both directions.

17. The device according to claim 1, further comprising positioning members configured to hold the lower limb of the seated subject stationary relative to a base of the device.

* * * * *

UNITED STATES PATENT AND TRADEMARK OFFICE
CERTIFICATE OF CORRECTION

PATENT NO. : 8,197,425 B2
APPLICATION NO. : 12/618096
DATED : June 12, 2012
INVENTOR(S) : Toshiki Kobayashi et al.

Page 1 of 1

It is certified that error appears in the above-identified patent and that said Letters Patent is hereby corrected as shown below:

In Claim 1, column 8, line 1, delete "complex, and" and insert -- complex and --.

In Claim 1, column 8, line 3, delete "computer" and insert -- computer software --.

In Claim 13, column 8, line 44, delete "$ROM_{ANKLE} > ROM_{AFO}$" and insert -- $ROM_{ANKLE} \geq ROM_{AFO}$ --.

Signed and Sealed this
Fourteenth Day of August, 2012

David J. Kappos
*Director of the United States Patent and Trademark Office*